United States Patent
Van Noy

(10) Patent No.: US 6,537,283 B2
(45) Date of Patent: Mar. 25, 2003

(54) INTRAOCULAR LENS SHIPPING CASE AND INJECTION CARTRIDGE

(75) Inventor: Stephen J. Van Noy, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 09/932,285

(22) Filed: Aug. 17, 2001

(65) Prior Publication Data
US 2003/0036765 A1 Feb. 20, 2003

(51) Int. Cl.$^7$ ................................................. A61F 9/00
(52) U.S. Cl. .............. 606/107; 414/416.04; 414/416.09
(58) Field of Search .................... 606/107; 221/188, 221/197, 198, 287; 414/416.04, 416.09; 604/11, 15, 16, 17, 294

(56) References Cited

U.S. PATENT DOCUMENTS

| | | |
|---|---|---|
| 3,744,493 A * | 7/1973 | Booher et al. ............... 604/62 |
| 4,487,865 A | 12/1984 | Balazs et al. |
| 4,500,676 A | 2/1985 | Balazs et al. |
| 4,573,998 A | 3/1986 | Mazzocco |
| 4,663,233 A | 5/1987 | Beavers |
| 4,681,102 A | 7/1987 | Bartell |
| 4,747,404 A | 5/1988 | Jampel et al. |
| 4,801,475 A | 1/1989 | Halpern et al. |
| 4,834,094 A | 5/1989 | Patton et al. |
| 4,836,201 A | 6/1989 | Patton et al. |
| 4,919,130 A | 4/1990 | Stoy et al. |
| 4,934,363 A | 6/1990 | Smith et al. |
| 4,959,074 A | 9/1990 | Halpern et al. |
| 5,007,913 A | 4/1991 | Dulebohn et al. |
| 5,023,114 A | 6/1991 | Halpern et al. |
| 5,037,677 A | 8/1991 | Halpern et al. |
| 5,190,552 A | 3/1993 | Kelman |
| 5,275,604 A | 1/1994 | Rheinish et al. |
| 5,304,182 A | 4/1994 | Rheinish et al. |
| 5,494,484 A | 2/1996 | Feingold |
| 5,499,987 A | 3/1996 | Feingold |
| 5,616,148 A | 4/1997 | Eagles et al. |
| 5,620,450 A | 4/1997 | Eagles et al. |
| 5,653,715 A | 8/1997 | Reich et al. |
| 5,653,753 A | 8/1997 | Brady et al. |
| 5,716,364 A | 2/1998 | Makker et al. |
| 5,728,102 A | 3/1998 | Feingold et al. |
| 5,735,858 A | 4/1998 | Makker et al. |
| 5,800,442 A | 9/1998 | Wolf et al. |
| 5,803,925 A | 9/1998 | Yang et al. |
| 5,810,834 A | 9/1998 | Heyman |
| 5,876,406 A | 3/1999 | Wolf et al. |
| 5,947,976 A | 9/1999 | Van Noy et al. |
| 6,010,510 A | 1/2000 | Brown et al. |
| 6,083,231 A | 7/2000 | Van Noy et al. |
| 6,143,001 A | 11/2000 | Brown et al. |
| 6,217,542 B1 * | 4/2001 | Stevens et al. ............... 604/17 |

FOREIGN PATENT DOCUMENTS

| | | |
|---|---|---|
| DE | 43 01 573 A | 7/1994 |
| GB | 2224214 A | 5/1990 |
| WO | WO 96/28122 A | 9/1996 |
| WO | WO 96/29956 | 10/1996 |
| WO | WO 97/15253 | 5/1997 |
| WO | WO 98/05281 A | 1/1998 |
| WO | WO 98/12969 A | 4/1998 |
| WO | WO 98/15244 | 4/1998 |
| WO | WO 00/62712 | 10/2000 |

* cited by examiner

Primary Examiner—Eduardo C. Robert
(74) Attorney, Agent, or Firm—Jeffrey S. Schira

(57) ABSTRACT

An intraocular lens cartridge having a distal injector portion and a proximal shipping portion. The injector portion and the shipping portion are join be a hinge that allows the shipping portion to be rotated so that the lens, when held in the shipping portion, aligns with the bore of the injector portion. The shipping portion may also be flexible so as to provide a prefold to the lens.

5 Claims, 5 Drawing Sheets

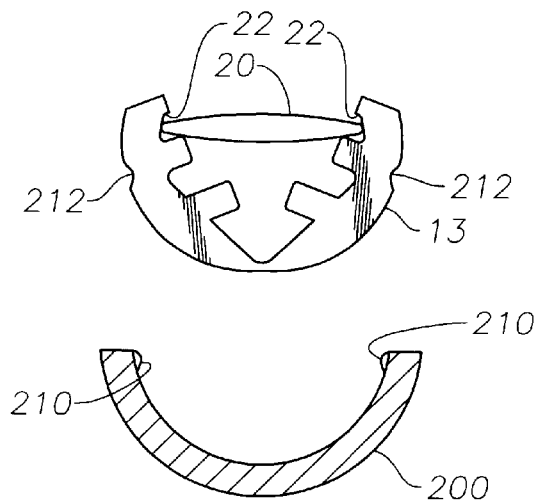
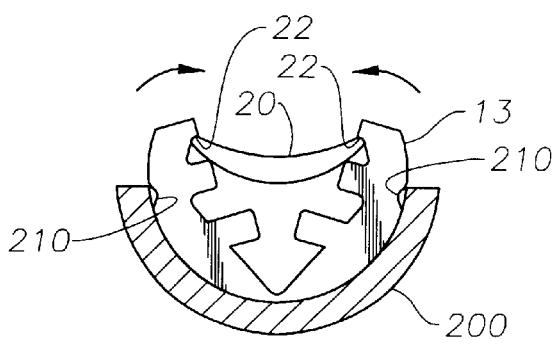
Fig. 5A
Fig. 5B
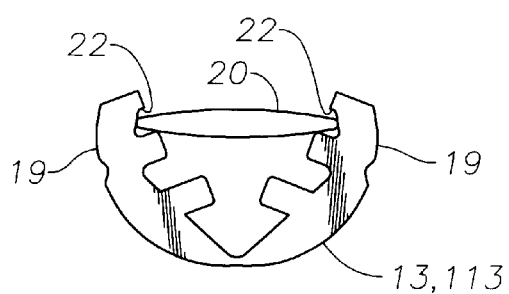
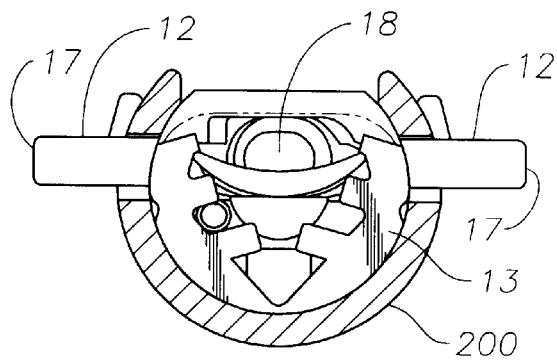
Fig. 6A
Fig. 5C
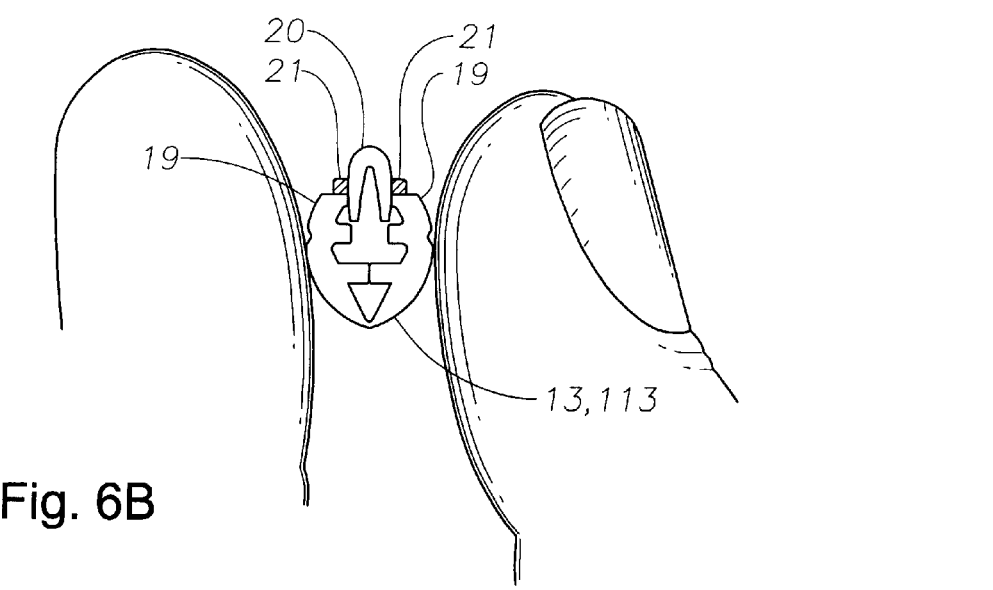
Fig. 6B

INTRAOCULAR LENS SHIPPING CASE AND INJECTION CARTRIDGE

This invention relates to intraocular lenses (IOLs) and more particularly to cases and cartridges used to ship and inject IOLs into an eye.

BACKGROUND OF THE INVENTION

The human eye in its simplest terms functions to provide vision by transmitting and refracting light through a clear outer portion called the cornea, and further focusing the image by way of lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmtharcrylate (PMMA), soft foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in U.S. Pat. No. 4,681,102 (Bartell), the entire contents of which is incorporated herein by reference, and includes a split, longitudinally hinged cartridge. Similar designs are illustrated in U.S. Pat. Nos. 5,494,484 and 5,499,987 (Feingold) and 5,616,148 and 5,620,450 (Eagles, et al.), the entire contents of which are incorporated herein by reference. In an attempt to avoid the claims of U.S. Pat. No. 4,681,102, several solid cartridges have been investigated, see for example U.S. Pat. No. 5,275,604 (Rheinish, et al.) and 5,653,715 (Reich, et al.), the entire contents of which are incorporated herein by reference.

These prior art cartridges are not suitable for sterilizing or shipping the IOL, and all currently available IOLs that use injection cartridge are shipped in a separate case and must be transferred to the cartridge prior to injection. This requires extra handling by the surgical staff in the operating room.

Accordingly, a need continues to exist for an IOL injector cartridge that can also be used as a shipping case.

BRIEF SUMMARY OF THE INVENTION

The present invention improves upon prior art injector cartridges by providing a cartridge having a distal injector portion and a proximal shipping portion. The injector portion and the shipping portion are join be a hinge that allows the shipping portion to be rotated so that the lens, when held in the shipping portion, aligns with the bore of the injector portion. The shipping portion may also be flexible so as to provide a prefold to the lens.

It is accordingly an object of the present invention to provide a lens injector cartridge that can be used to both ship the lens and inject the lens into the eye.

It is a further object of the present invention to provide a lens injector cartridge that generally folds the lens.

It is a further object of the present invention to provide a lens injector cartridge that minimizes the potential for damage to the optics and/or the haptics.

Another objective of the present invention is to provide a lens injection cartridge having a distal injector portion and a proximal shipping portion.

Other objects, features and advantages of the present invention will become apparent with reference to the drawings, and the following description of the drawings and claims.

BRIEF DESCRIPTION OF THE DRAWINGS

FIGS. 5A–5C are rear elevational views of the shipping portion of the cartridge of the present invention being installed into a handpiece.

FIGS. 6A–6B are rear elevational views of the shipping portion of the cartridge of the present folding a lens manually.

DETAILED DESCRIPTION OF THE INVENTION

Figure 1A:
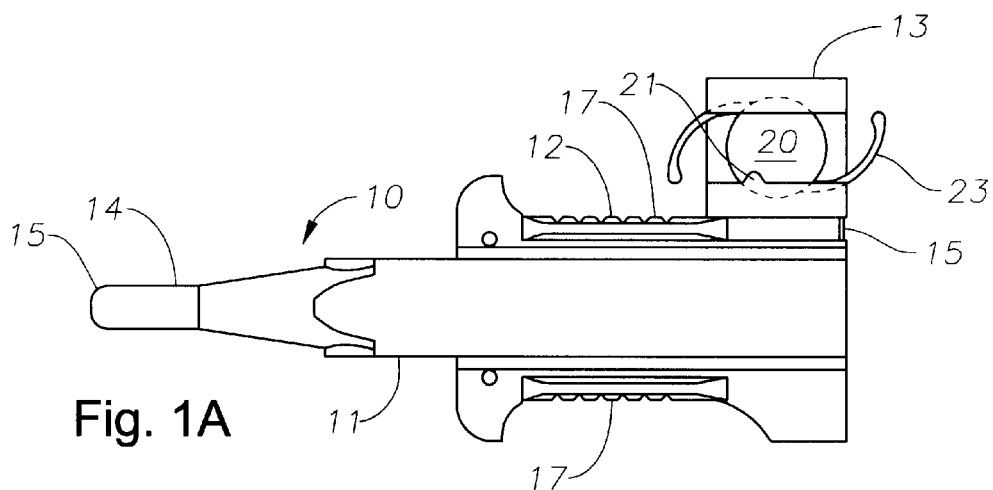
FIGS. 1A–1C are top plan views of a first embodiment of the cartridge of the present invention.
Figure 1B:
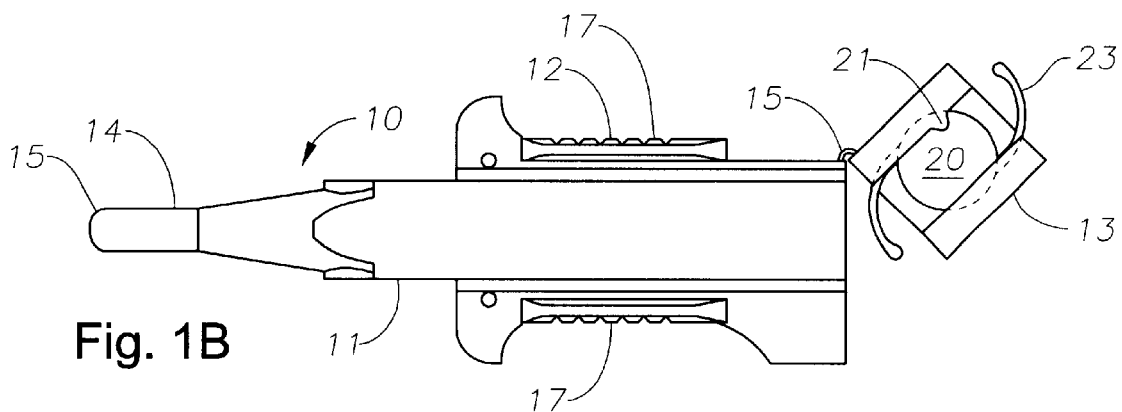
Figure 1C:
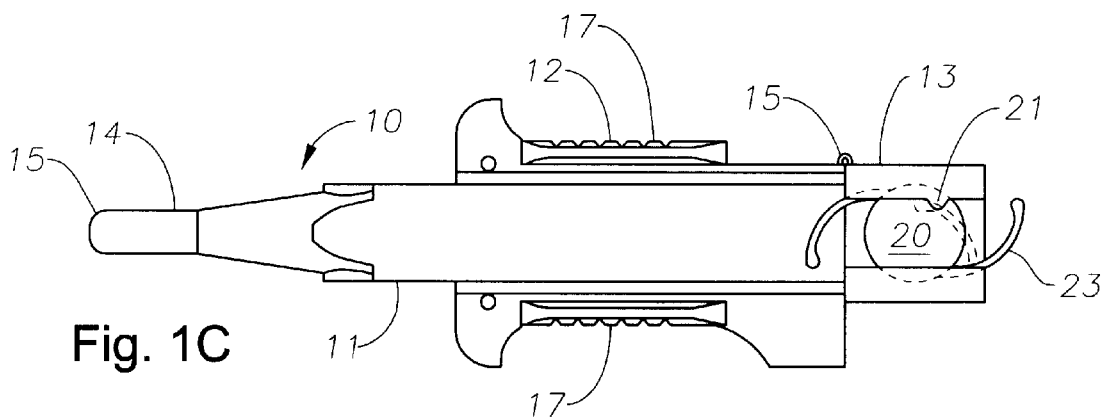

As best seen in FIGS. 1A–1C and 2A–2B, intraocular lens injector cartridge 10 and 110 of the present invention generally has injector portion 11, and 111 and shipping portion 13 and 113. Injector portion 11 and 111 generally include tubular body 12 and 112 and injection nozzle 14 and 114, respectively. Injector portion 11 and 111 and shipping portion 13 and 113 are connected by hinge 15 and 115, respectively. Cartridge 10 and 110 preferably are molded as a single piece from any suitable thermoplastic, such as polyproplyene, and the thermoplastic may contain a lubricity enhancing agent such as those disclosed in U.S. Pat. No. 5,716,364, the entire contents of which are incorporated herein by reference. Nozzles 14 and 114 preferably are rounded, oval or elliptical in cross-section and has a cross-sectional area of preferably between 1.0 mm$^2$ to around 6.5 mm$^2$ at distal tip 15 and 115. Distal tip 15 and 115 of nozzle 14 and 114 preferably is rounded on the interior and exterior. Body 12 and 112 preferably contain grips 17 and 117 that allow easier manipulation of cartridge 10 and 110 and provide a mechanism to lock cartridge 10 and 110 in the injection handpiece 200. Suitable designs for injector portion 11 and 111 of cartridge 10 and 110 are illustrated in U.S. Pat. Nos. 5,947,976, 6,083,231 and 6,143,001, the entire contents of which are incorporated herein by reference. Shipping portion 13 may contain ridge or protuberance 21 that allows for the folding or tucking of trailing haptic 23 over IOL 20, as seen in FIG. 1C.

In order to facilitate further the movement of IOL 20 down bore 18, interior surface 19 of bore 18 may be coated with a lubricous coating such as those described in U.S. Pat. Nos. 4,487,865, 4,500,676, 4,663,233, 4,801,475, 4,959,074, 5,023,114 and 5,037,677, the entire contents of which are incorporated herein by reference. Bore 18 may also be coated by any commercially available medical grade viscoelastic, such a VISCOAT® viscoelastic available from Alcon Laboratories, Inc., Fort Worth, Tex. The inventors have also found that texturizing interior surface 19 also assists in the movement of IOL 20 down bore 18 by minimizing the amount of surface contact between interior surface 19 and IOL 20 and by entrapping any viscoelastic agent between interior surface 19 and IOL 20. For example, a surface roughness of greater than 0.45 microns RMS may be used. Such a finish can be generated by a two step process incorporating an initial random pattern texture by sandblasting or acid etching followed by a specific directional polish along the longitudinal axis of bore 18 in order to achieve a cropped or plateau effect.

Figure 2A:
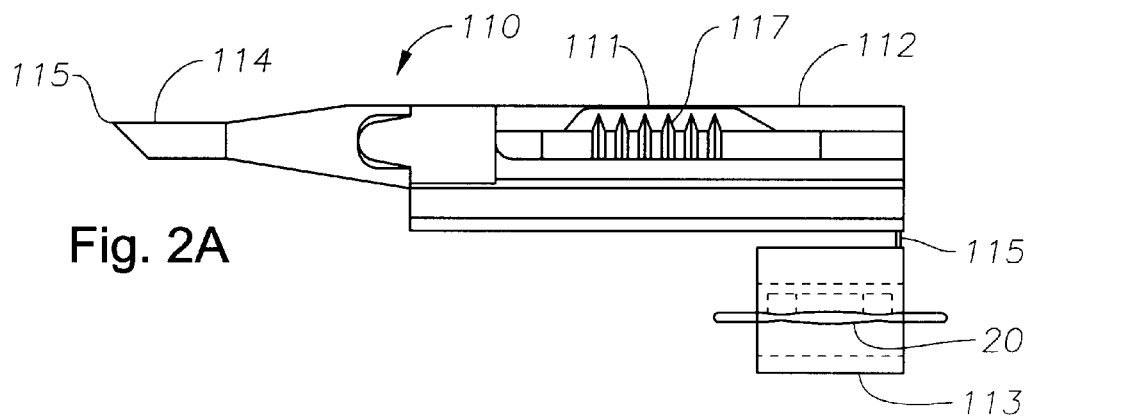
FIGS. 2A–2C are side elevational views of a second embodiment of the cartridge of the present invention.
Figure 2B:
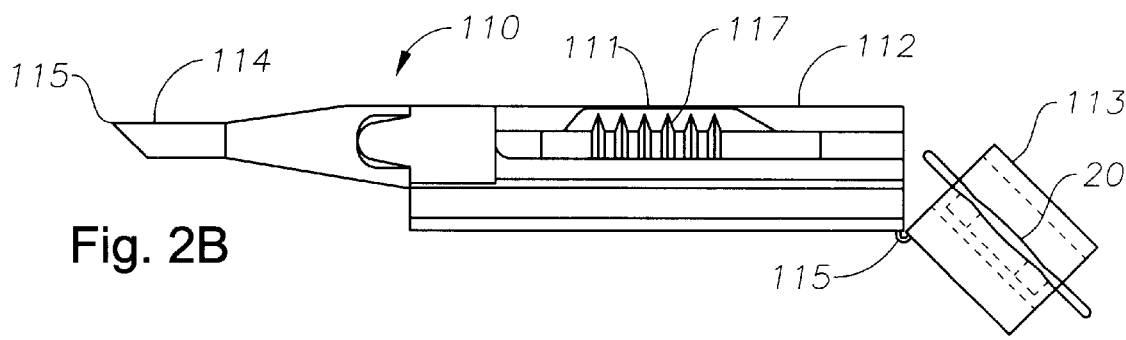
Figure 2C:
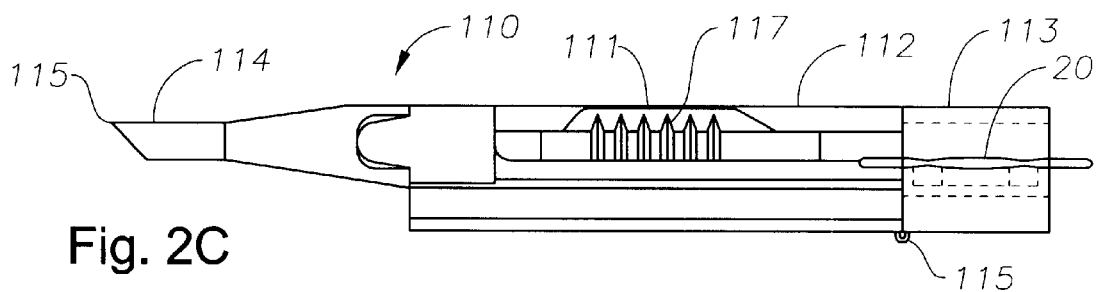
Figure 3:
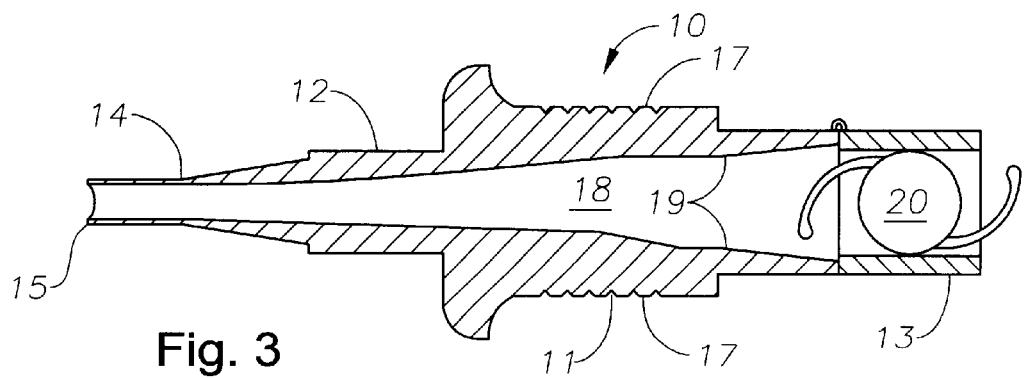
FIG. 3 is a cross-sectional view of the first embodiment of the cartridge of the present invention.
Figure 4A:
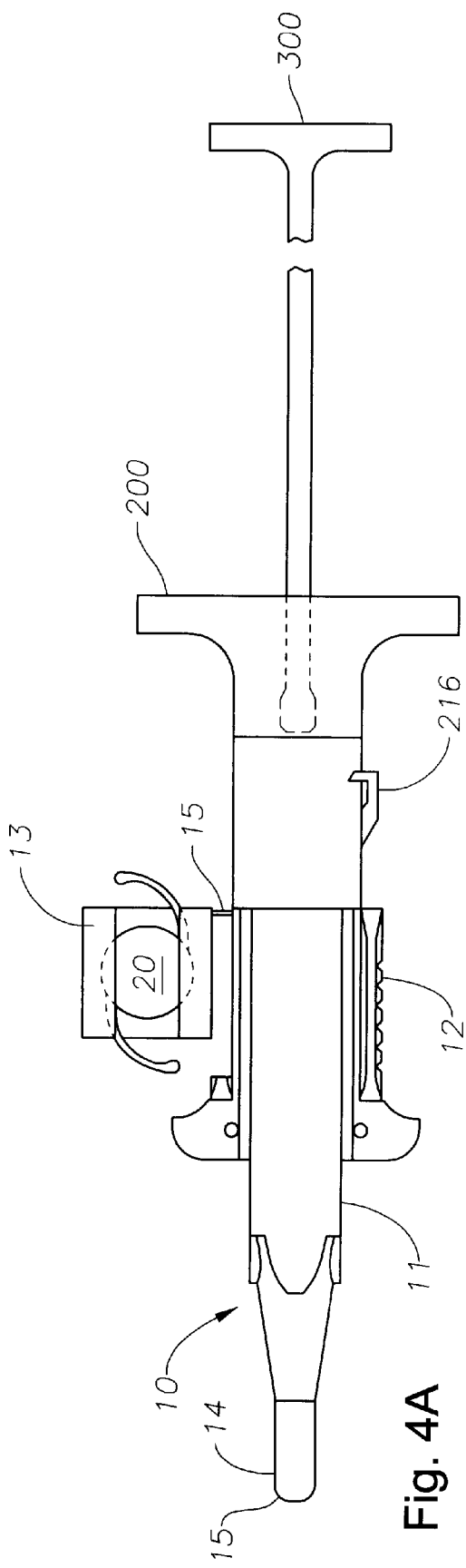
FIGS. 4A–4D are a top plan views of one embodiment of the cartridge/handpiece combination of the present invention delivery a lens.
Figure 4B:
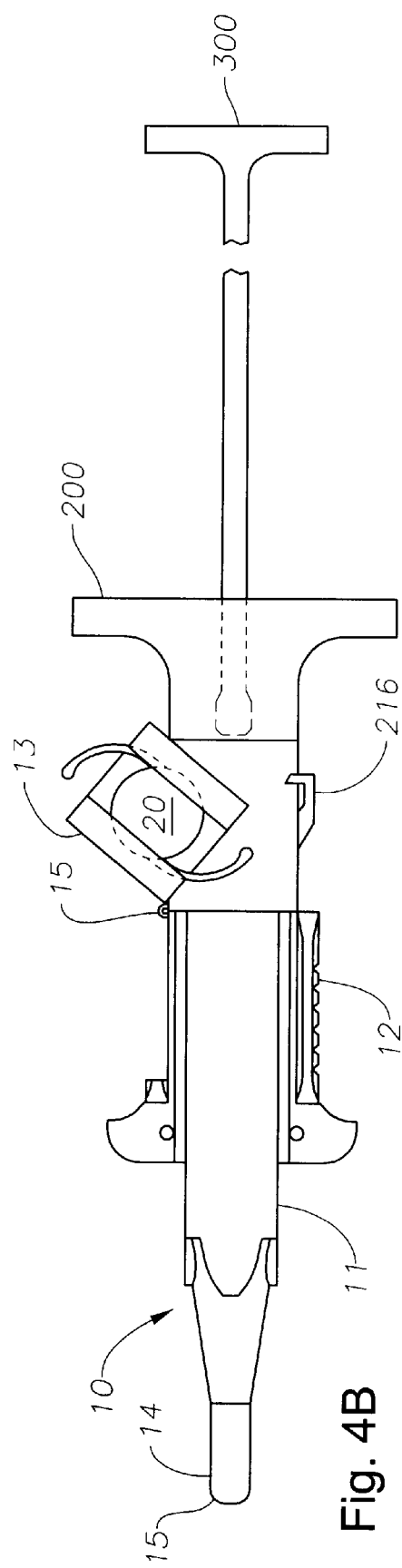
Figure 4C:
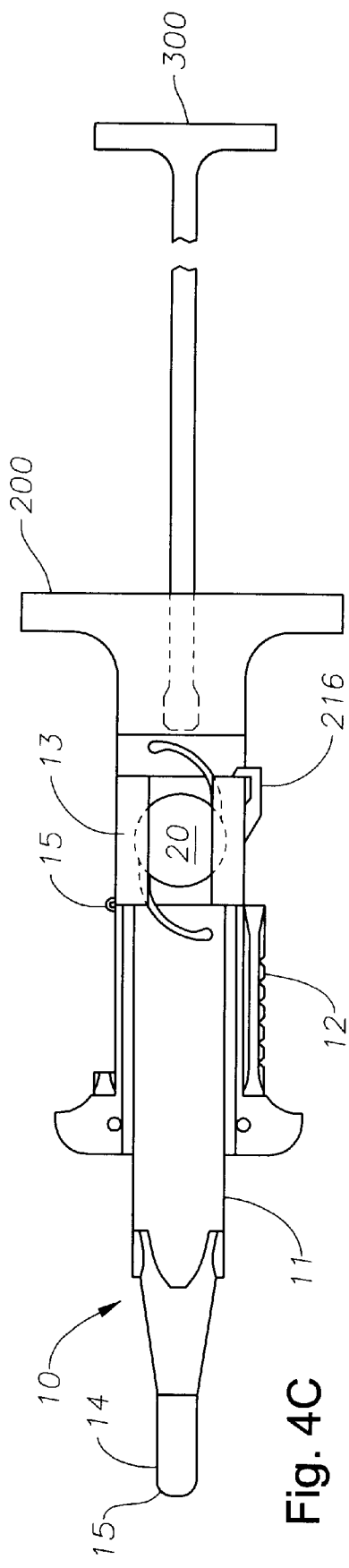
Figure 4D:
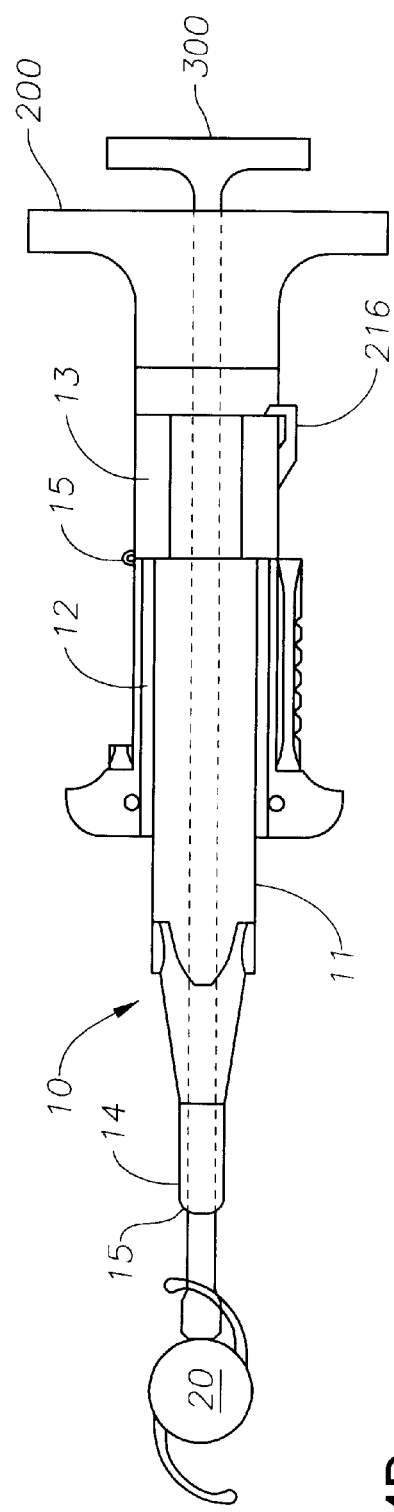

As best seen in FIGS. 5A–5B, shipping portion 13 (and shipping portion 113, not shown) is design so as to hold IOL 20 firmly and in a relatively relaxed state during sterilization and shipping, for example, by the use of sockets 22. As best seen in FIGS. 1 and 2, when shipping portion 13 and 113 are rotated about hinge 15 and 115, respectively, IOL 20 aligns with bore 18 in body 12 of cartridge 10, and with the bore (not shown) in body 112 of cartridge 110. Cartridge 10 or 110 may then be loaded into handpiece 200. As best seen in FIGS. 5A–5C, handpiece 200 may contain tabs 210 that align with detents 212 in shipping portion 13 so as to collapse partially shipping portion 13 and hold lens 20 in a slightly pre-folded condition. Additional folding occurs as lens 20 travels down tapering nozzle 11 or 114. As best seen in FIGS. 4A–4D, lens 20 may then be easily pushed through cartridge 10 or 110 by plunger 300 of handpiece 200 and expressed out distal tip 15 of nozzle 14 (or distal tip 115 of 114). Handpiece 200 may contain a feature, such as clasp 216 that hold shipping portion 13 or 113 tightly against shipping portion 11 or 111, respectively. As shown in FIGS. 4A–4D, cartridge 10 or 110 and handpiece 200 may be integrally made as a single piece injector. Alternatively, cartridge 10 and 110 may be made separately from handpiece 200, as shown in FIGS. 1–3, with handpiece 200 being any suitable design, such as that shown in U.S. Pat. No. 6,010,510, the entire contents of which being incorporated herein by reference.

As best seen in FIGS. 6A–6B, shipping portion 13 or 113 may alternatively be used to fold lens 20 manually, without the use of handpiece 200, by squeezing together sides 19 of shipping portion 13 or 113 so as to fold lens 20. Folded lens 20 may then be removed by forceps 21.

While certain embodiments of the present invention have been described above, these descriptions are given for purposes of illustration and explanation. Variations, changes, modifications, and departures from the systems and methods disclosed above may be adopted without departure from the scope or spirit of the present invention.

I claim:

1. An intraocular lens injector cartridge, comprising:
   a) an injector portion suitable for injecting an intraocular lens into an eye; and
   b) a shipping portion, the shipping portion being connected to the injector portion by a hinge,
   wherein the shipping portion holds the lens in a first position during shipping and the shipping portion may be pivoted about the hinge to a second position for allowing the lens to be delivered to the injector portion.

2. The cartridge of claim 1, wherein the injector portion and the shipping portion are integrally formed.

3. An intraocular lens injector cartridge, comprising:
   a) an injector portion having a bore and suitable for injecting an intraocular lens into an eye; and
   b) a shipping portion, the shipping portion being connected to the injector portion by a hinge,
   wherein the shipping portion holds the lens in a first position during shipping and the shipping portion may be pivoted about the hinge to a second position wherein the lens is aligned with the bore.

4. An intraocular lens injection system, comprising:
   a) a handpiece containing a plunger; and
   b) an injector cartridge, the cartridge sized and shaped to be received in the handpiece and having an injector portion suitable for injecting an intraocular lens into an eye and a shipping portion, the shipping portion being connected to the injector portion by a hinge,
   wherein the shipping portion holds the lens in a first position during shipping and the shipping portion may be pivoted about the hinge to a second position for allowing the lens to be delivered to the injector portion.

5. An intraocular lens injection system, comprising:
   a) a handpiece containing a plunger; and
   b) an injector cartridge integrally formed with the handpiece, the cartridge having an injector portion suitable for injecting an intraocular lens into an eye and a shipping portion, the shipping portion being connected to the injector portion by a hinge,
   wherein the shipping portion holds the lens in a first position during shipping and the shipping portion may be pivoted about the hinge to a second position for allowing the lens to be delivered to the injector portion.

* * * * *